United States Patent
Middleton

(10) Patent No.: US 7,312,083 B2
(45) Date of Patent: Dec. 25, 2007

(54) CONTROL VALUE ASSIGNMENT METHOD

(75) Inventor: John S. Middleton, Fullerton, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 410 days.

(21) Appl. No.: 11/147,584

(22) Filed: Jun. 7, 2005

(65) Prior Publication Data

US 2006/0275908 A1 Dec. 7, 2006

(51) Int. Cl.
*G01N 31/00* (2006.01)
*G01N 33/48* (2006.01)

(52) U.S. Cl. .............. 436/8; 436/63; 436/73; 436/74; 436/80; 436/149; 436/164; 702/19

(58) Field of Classification Search ............ 436/8, 436/63, 73, 74, 79, 80, 81, 97, 98, 149, 150, 436/164, 901, 909; 702/19
See application file for complete search history.

(56) References Cited

U.S. PATENT DOCUMENTS

| | | | | |
|---|---|---|---|---|
| 4,202,033 A | | 5/1980 | Strobel | 364/416 |
| 4,618,587 A | | 10/1986 | Premoli et al. | 436/74 |
| 5,667,983 A | * | 9/1997 | Abel et al. | 435/14 |
| 5,789,249 A | | 8/1998 | Eisum | 436/8 |
| 6,372,503 B1 | * | 4/2002 | Samsoondar | 436/8 |
| 6,703,241 B1 | | 3/2004 | Sunshine et al. | 436/8 |
| 7,157,282 B2 | * | 1/2007 | Samsoondar | 436/8 |
| 7,172,902 B2 | * | 2/2007 | Samsoondar | 436/8 |
| 2002/0055175 A1 | | 5/2002 | Casal et al. | 436/55 |

OTHER PUBLICATIONS

Baadenhuijsen et al. (abstract) Annals of Clinical Biochemistry, vol. 37, No. 3, May 1, 2000, pp. 330-337.*
P. M. Broughton; L. Eldjarn; *Methods of assigning accurate values to reference serum. Part 1. The use of reference laboratories and consensus values, with an evaluation of a procedure for transferring values from one reference serum to another*, Ann Clin Biochem. Nov. 1985; 22 (Pt 6): 625-34.
L. Eldjarn; P.M. Broughton; *Methods of assigning accurate values to references serum. Part 2. The use of definitive methods, reference laboratories, transferred values and consensus values*, Ann Clin Biochm. Nov. 1985:22 (Pt 6):635-49.
C. Franzini, *Commutability of reference materials in clinical chemistry*, J. Int. Fed. Clin. Chem. Sep. 1993; 5(4): 169-73.
A.B. Sigalov, *Comparison of apolipoprotein A-1 values assayed in lyophilized and frozen pooled human sera by a non-immunochemical electrophoretic method and by immunoassay*, Eur. J. Clin. Chem. Clin. Biochem. Sep. 1993:31(9): 579-83.
Emmanuel Brion, et al., Evaluation of Commutability of Control Materials, Clin Chem Lab Med 2002; 40(6): 625-630.

* cited by examiner

*Primary Examiner*—Maureen M. Wallenhorst
(74) *Attorney, Agent, or Firm*—Jeffrey G. Sheldon; Sheldon Mak Rose & Anderson PC

(57) ABSTRACT

A method of assigning expected recovery values to control substances used in analytical testing is disclosed.

19 Claims, 2 Drawing Sheets

CONTROL VALUE ASSIGNMENT METHOD

BACKGROUND

Figure 1:
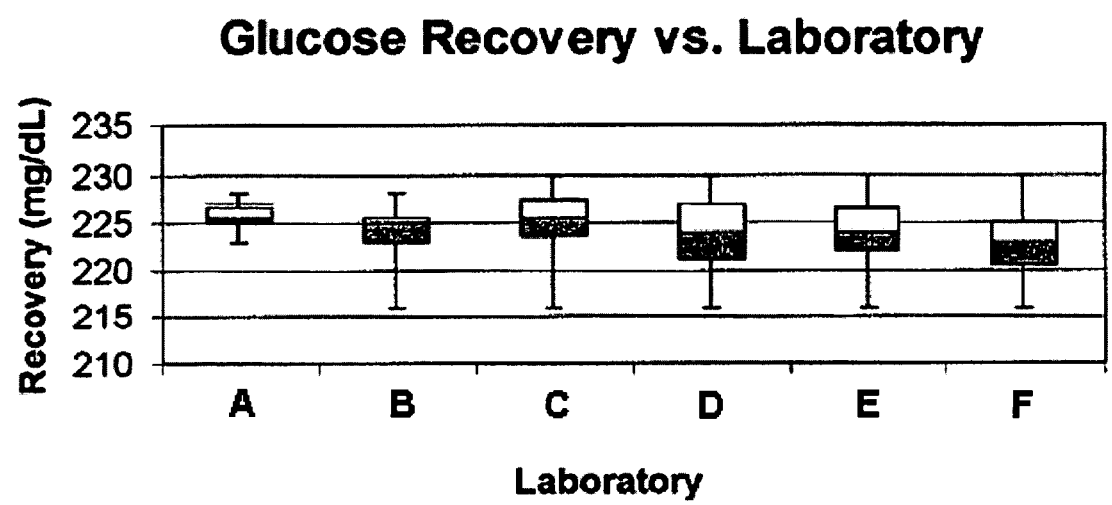

Controls are used in analytical testing in order to provide a reference against which experimental results can be compared. In order to act as a referent, a control material is subjected to the same or similar conditions as a sample material to be tested. The ability to compare experimental results with the results of measuring a control material enables the assessment of the significance of the experimental results.

The precise amount of an analyte detected in a control material can change depending on the particular analytical instrument used to assay the control material, as well as on the particular chemical reaction to which the control material is subjected in order to measure the analyte. To determine the amount of an analyte which a user can expect to detect in a control material (the recovery value) with a particular analytical instrument using a particular chemical method, a control substance is typically tested independently with that instrument and method by a number of different laboratories (see, e.g., Brion, E., et al., "Evaluation of Commutability of Control Materials," Clin Chem Lab Med, 40:625-630 (2002)). The target recovery value for the control is then assigned based on an average of the values determined by such laboratories.

SUMMARY

The present method of determining an expected recovery value for an analyte in a control material allows accurate analyte recovery values to be assigned with less laboratory testing, thereby saving both time and expense in the value assignment process. This method includes the step of determining a relative analyte concentration ratio. This ratio is determined by measuring the amount of the analyte in a control sample using a first methodology, i.e. an analytical procedure or method performed with a certain analytical instrument, to obtain a first control sample concentration value. A second control sample concentration value determined using a second methodology is also obtained, and the first control sample concentration value is added to the second control sample concentration value to determine a summed control sample concentration value. The first control sample concentration value is then divided by the summed control sample concentration value to obtain the relative analyte concentration ratio.

The present method further includes the step of determining a summed target sample concentration value. In this step, a first target sample concentration value is obtained by measuring the amount of the analyte in the target sample using the first methodology, and a second target sample concentration value is determined by measuring the amount of the analyte in the target sample using the second methodology. The first target sample concentration value is then added to the second target sample concentration value to obtain the summed target sample concentration value. Once the relative analyte concentration ratio and summed target sample concentration value have been obtained, the assigned value for the analyte in the target sample can be determined by multiplying the relative analyte concentration ratio by the summed target sample concentration value.

The present method, in one embodiment, can further comprise the steps of obtaining a third control sample concentration value by measuring the amount of the analyte in the control sample using a third methodology, in which case the summed control sample concentration value comprises the sum of the first control sample concentration value, the second control sample concentration value, and the third control sample concentration value. In this embodiment, a third target sample value is also obtained by measuring the amount of the analyte in the target sample using the third methodology, and the summed target sample concentration value in this case likewise comprises the sum of the first target sample concentration value, the second target sample concentration value, and the third target sample concentration value.

The first control sample concentration value is preferably an average of a plurality of values determined by measuring the amount of the analyte in the control sample a plurality of times using the first methodology. The analyte in the control sample is also preferably measured by a plurality of different testers, such as by at least six different testers.

Various combinations of analytical methods and instruments can be used in the present method. For example, the first and second methodologies can comprise a single analytical method performed on two different analytical instruments. Alternatively, the first and second methodologies can comprise two different analytical methods performed on the same analytical instrument. The first and second methodologies can also comprise different, non-overlapping analytical instruments and methods rather than sharing a common method or instrument. The analytical methods used in the present method can include, for example, optical detection methods, nephelometric methods, or electrochemical methods. The analytical instruments can be a spectrophotometer, a colorimeter, a nephelometer, a polarimeter, a potentiometer, a voltmeter, and/or a fluorometer.

The target sample in the present method can be any of a number of materials, such as urine, plasma, serun, blood, saliva, or cerebrospinal fluid. The analyte for which a recovery value is to be determined can likewise be any of a number of analytes for which testing is performed, including albumin, alanine aminotransferase, amylase, aspartate transferase, alkaline phosphatase, blood urea nitrogen, calcium, cholesterol, high-density lipoprotein cholesterol, creatinine kinase, creatinine, bilirubin, gamma-glutamyl transferase, glucose, iron, lactate dehydrogenase, magnesium, phosphorous, total iron binding capacity, total bilirubin, total protein, triglyceride GPO, uric acid, digoxin, gentamicin, phenobarbital, phenyloin, salicylate, theophylline, tobramycin, alcohol, ammonia, anti-streptolysin-O, cholinesterase, C-reactive protein, alpha-hydroxybutyrate dehydrogenase, lactate, leukocyte alkaline phosphatase, microprotein, pancreatic amylase, chloride, $CO_2$, potassium, sodium, IgA, IgG, IgM, transferrin, thyroxine, thyroxine-uptake, acetaminophen, acid phosphatase, amikacin, amphetamine, barbiturate, cannabinoid, carbamazepine, cocaine, ethosuximide, fibrinogen, fructosamine, lactate dehydrogenase-1, lidocaine, lipase, methadone, methaqualone, N-acetylprocainamide, opiate, phencyclidine, primidone, procainamide, propoxyphene, quinidine, valproic acid, and vancomycin.

DRAWINGS

These and other features, aspects and advantages of the present invention will become better understood with regard to the following description, appended claims, and accompanying figures where:

FIG. 1 is a graph depicting the amount of glucose measured at different laboratories when testing for the concentration of glucose in a control material (Synchron Control Comprehensive Chemistry Control Serum, available from Beckman Coulter, Inc., Fullerton, Calif.) with a SYNCHRON LX clinical system (available from Beckman Coulter, Inc., Fullerton, Calif.) using a glucose oxidase test.

Figure 2:
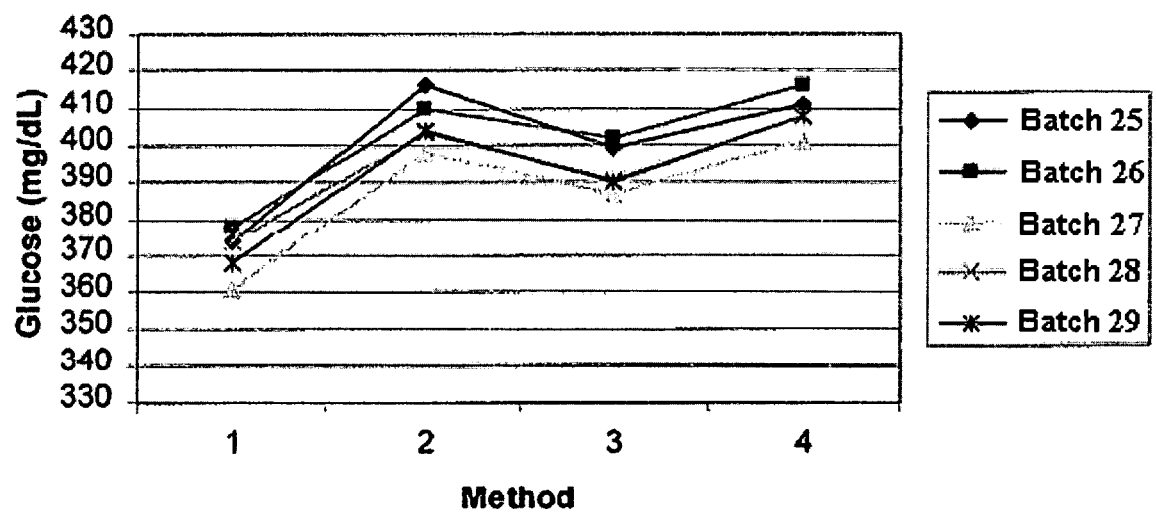

FIG. 2 is a graph showing the relationships between the glucose values obtained for 5 batches of Synchron Control Comprehensive Chemistry Control Serum (Synchron Control) measured with 2 different analytical instruments, a SYNCHRON LX clinical system and a SYNCHRON CX clinical system (available from Beckman Coulter, Inc., Fullerton, Calif.), using two different analytical methods (a glucose oxidase test and a glucose hexokinase test).

All dimensions specified in this disclosure are by way of example only and are not intended to be limiting. Further, the proportions shown in these Figures are not necessarily to scale. As will be understood by those with skill in the art with reference to this disclosure, the actual dimensions of any device or part of a device disclosed in this disclosure will be determined by their intended use.

DESCRIPTION

The present method allows a reduced number of tests to be performed when assigning recovery values to control materials compared to prior methods. Another aspect of the present method is that with a limited data set, the present method can generate more accurate analyte recovery values compared with prior methods. Currently, for each batch of a control material having an analyte whose concentration is to be determined, and for each methodology used to assess this analyte, multiple tests are performed using the particular methodology, generally at a number of different laboratories. FIG. 1 illustrates this approach, showing the results of testing at six different laboratories of a batch of Synchron Control material using a SYNCHRON LX instrument and a glucose oxidase test, with the boxed areas showing the middle 50% of the data and the lines showing the range of all data. The expected recovery value for the analyte (glucose) that is assigned to this batch of control material, when using a SYNCHRON LX instrument and performing a glucose oxidase test, is the average of the analyte recovery values determined from testing performed at these different laboratories, i.e. the average of all of the individual measurements obtained. An expected recovery value can be obtained, for example, by performing at least six tests at 6 different labs.

Each time a new batch of control material is produced, it must be tested in this way in order to assign an expected recovery value for analyte in the material, according to prior methods. However, it has now been determined that analyte recovery values measured using different methodologies exhibit consistent relationships, and in the present methods these relationships are used to predict analyte recovery values based on more limited testing. The present method therefore saves both time and expense compared with the prior art.

Definitions

As used herein, the following terms and variations thereof have the meanings given below, unless a different meaning is clearly intended by the context in which such term is used.

"Control" or "control material" refers to a material which is analyzed in order to accurately determine its composition, at least with respect the identity and concentration of an analyte in the material. A control can be measured by an analytical instrument, and such measurement can be compared with a measurement of a sample of unknown or incompletely determined composition taken by the same instrument.

"Batch" refers to a defined quantity of product, such as a control material, which is accumulated under conditions considered uniform for sampling purposes. A batch of control is produced with a defined set of starting materials over a limited period of time.

"Methodology" refers to an analytical procedure or method performed with a certain analytical instrument. The analytical instrument can be a particular class, model or type of instrument. An analytical procedure can include subjecting a sample to a chemical reaction and then analyzing the reaction products. For purposes of the present definition, the performance of the same analytical procedure with a different analytical instrument, or the performance of a different analytical procedure with the same analytical instrument, constitutes the performance of a different methodology.

"Tester" refers to an individual or group performing a methodology. Different groups can, for example, comprise different clinical laboratories, usually in different locations.

The term "comprise" and variations of this term, such as "comprising" and "comprises," are not intended to exclude other additives, components, integers or steps. The terms "a," "an," and "the" and similar referents used herein are to be construed to cover both the singular and the plural unless their usage in context indicates otherwise.

Materials

Any of a number of materials used as controls in analytical tests can have values assigned to them using the present methods. Preferably, the controls are used in a diagnostic assay for evaluating the medical condition of a human or animal subject, for example to diagnose a disease or other medical condition, to determine whether the subject is at risk for developing a medical condition, or to monitor a medical condition or a risk factor for developing a condition. The control material used in diagnostic assays can comprise or be derived from a biological substance such as urine, plasma, serum, blood, saliva, or cerebrospinal fluid. For example, a standardized serum preparation such as Synchron Control can be used as a control material in a diagnostic assay.

Medical conditions evaluated using diagnostic assays include, for example, anemia, autoimmune disease, cardiac function and disease, hepatic function and disease, renal function and disease, infectious disease, inflammatory conditions, and nutritional status. A list of some analytes detected to evaluate medical conditions which can be present in control materials is given in Table 1 below.

TABLE 1

Control Material Analytes

| Anemia | Cardiac Disease | Hepatic Disease | Renal Disease | Diabetes | Nutritional Status | Additional Indicators |
|---|---|---|---|---|---|---|
| iron | creatine kinase (CK) | albumin | albumin | glucose | albumin | amylase |
| total iron binding capacity (TIBC) | CK-MB | alanine amino- transferase (ALT) | angiotensinogen converting enzyme (ACE) | HbA1c | prealbumin | magnesium, potassium, sodium, chloride |
| haptoglobin | digoxin | aspartate transferase (AST) | calcium | HbA1c2 | transferrin | $CO_2$ |
| transferrin | C-reactive protein (CRP) | alkaline phosphatase (ALP) | blood urea nitrogen (BUN) | HDL | | lactate dehydrogenase |
| | homocysteine | gamma- glutamyl transferase (GGT) | creatinine | LDL | | pancreatic amylase |
| | total cholesterol | prealbumin | microalbumin | microalbumin | | lipase |
| | high-density lipoprotein (HDL) | IgA | phosphorous | total protein | | uric acid, urea |
| | low-density lipoprotein (HDL) | IgG | | triglyceride | | cholinesterase |
| | triglyceride | IgM | | | | C3, C4 |
| | APO-A | total bilirubin | | | | fibrinogen |
| | APO-B | direct bilirubin | | | | ammonia |
| | | total protein | | | | anti- streptolysin-O |

The presence or concentration of drugs of abuse, medications, or other therapeutic substances can also be detected or monitored with diagnostic assays. Analytes detected to evaluate the use of drugs of abuse include, for example, alcohol, amphetamine, barbiturates, benzodiazepine, cannabinoid, cocaine, lidocaine, methadone, methaqualone, opiates, phencyclidine, and propoxyphene. Therapeutic substances which can be monitored using diagnostic assays include, inter alia, acetaminophen, carbamazepine, cyclosporine, gentamicin, lithium, phenobarbital, phenyloin, tobramycin, salicylate, theophylline, thyroxine, valproic acid, and vancomycin.

Reagents known to the art for evaluating analytes in control materials such as those listed above can be used in the present methods. Such reagents include, for example, bromcresol purple, Trinder's reagent, picrate, hexokinase, glucose oxidase, lactate oxidase, peroxidase, uricase, quinolinium dye, arsenazo III, ferrozine, pyridylazo dye, calmagite, formazan dye, molybdate, p-methylaminophenol, 2-amino-2-methyl-1-propanol, 2-chloro-4-nitrophenylmaltotrioside, dye amylopectin, monothioglycerol, N-acetylcysteine, pyruvate-lactate, and diglyceride.

Analytical instruments known to the art can be used in the present methods to detect analytes in control materials. Such instruments include, for example, spectrophotometers, colorimeters, nephelometers, polarimeters, radioimmunoassay instruments, potentiometers, voltmeters, and fluorometers. In one embodiment, a system combining a plurality of different types of analytical instruments can be used. For example, the SYNCHRON LX and SYNCHRON CX clinical systems include, inter alia, a spectrophotometer and a potentiometer in order to measure analyte concentrations.

Methods

In the present methods, recovery values for an analyte in a control material are first obtained using at least two methodologies. In preferred embodiments, three or more methodologies can be used. To obtain a recovery value for the analyte glucose in a control material, for example, the control is contacted with a glucose oxidase solution (such as the GLUCm glucose reagent, product number 472500, provided for the SYNCHRON LX clinical system and available from Beckman Coulter, Inc., Fullerton, Calif.), and the rate of oxygen consumption is measured with an oxygen electrode provided with an analytical instrument such as a SYNCHRON LX clinical system. The peak rate of oxygen consumption is directly proportional to the concentration of glucose in the sample. In another methodology, glucose can be measured by reacting the control sample with glucose hexokinase (such as GLU glucose reagent, product number 442640, provided for the SYNCHRON LX clinical system and available from Beckman Coulter, Inc., Fullerton, Calif.), and then measuring the reaction products with a spectrophotometer provided with an analytical instrument such as a SYNCHRON LX clinical system. The amount of glucose measured using each of these two methods and the single analytical instrument would constitute analyte recovery values from two methodologies. Alternatively, the second methodology can comprise, for example, reacting glucose with glucose oxidase and measuring the reaction products with a different instrument, such as a SYNCHRON CX clinical system. As will be apparent to one of skill in the art, the present methods are general and not limited to the use of these particular methodologies.

Once analyte recovery values are determined for such a control sample using at least two different methodologies, the relationships between the recovery values can next be determined. Such relationships, referred to as inter-method relationships, have been found to be stable over time, despite batch-to-batch variation in the absolute concentrations of an analyte recovered using particular methodologies. These inter-method relationships allow analyte recovery values for control materials to be accurately estimated with limited data.

The analyte recovery values determined using a particular methodology can be determined either through single measurements or through averaging multiple measurements. The determination of whether a single measurement using a particular methodology is appropriate for use in the present methods depends on the accuracy of single measurements using such methodology. If a plurality of measurements is required to obtain an accurate value using a particular methodology, one of skill in the art will be able to determine the number of tests to be performed, such as by performing several tests and determining whether the standard deviation of the measurements obtained from such testing is within an appropriate range. Performing additional tests using a particular methodology and using such test results in obtaining an average value can ensure more accurate recovery values in some cases. When multiple tests are performed, using different testers, preferably in different laboratories or locations, to perform such tests can also increase accuracy.

After determining analyte recovery values using at least two methodologies, such values are summed (i.e. added together). The relative analyte recovery ratio determined by a particular methodology is then calculated by dividing the analyte recovery value determined by that methodology by the summed analyte recovery values. For example, the relative analyte recovery ratio for the glucose hexokinase/SYNCHRON LX methodology in the example described above would be the glucose hexokinase/SYNCHRON LX recovery value divided by the sum of the analyte recoveries measured using the glucose hexokinase/SYNCHRON LX methodology and the glucose oxidase/SYNCHRON LX methodology.

The relative analyte recovery ratio for the analyte can be used to estimate an expected recovery value in a further sample of control material, which shall be referred to as the target sample. The target sample is subjected to the same methodologies to which the control sample was subjected, and an analyte recovery value is determined for the target sample with each of these methodologies. An expected recovery value for the analyte in the target sample using a particular methodology can then be assigned by adding together the recovery values found using each of the methodologies, and then multiplying that sum by the relative analyte recovery ratio determined previously for that methodology. For example, using the example described above, the relative analyte recovery ratio for the control sample using the glucose hexokinase/SYNCHRON LX methodology can be multiplied by the sum of the recovery values for the target sample determined using the glucose hexokinase/SYNCHRON LX and the glucose oxidase/SYNCHRON LX methodologies. The resulting number is the recovery value to be assigned to the target sample for the analyte when it is measured using the glucose hexokinase/SYNCHRON LX methodology.

The present methods are particularly advantageous when obtaining an accurate analyte recovery value using a particular methodology would otherwise require the measurement of a target sample a plurality of times and/or with a plurality of testers. In this case the number of measurements needed to determine an accurate recovery value for the analyte in the target sample can be greatly reduced. For example, if a control sample is evaluated through the performance of 36 tests by six different laboratories to determine an analyte recovery value for each of two different methodologies using prior methods, the expected concentration of the analyte recovered when a target sample is tested using those two methodologies can be accurately estimated by performing only 24 tests on the target sample using each of the methodologies and then employing the present method of determining expected recovery values. Advantageously, historical data which has already been generated in order to determine an accurate recovery value for an analyte in a control sample can be used in the present methods, allowing future analyte recovery data to be generated with less testing.

EXAMPLES

Example 1

Inter-Method Relationships

The amounts of glucose present in Synchron Control materials were measured using two different chemical methods, a glucose oxidase test and a glucose hexokinase test. Each of these tests was performed on two different analytical instruments, a SYNCHRON LX and SYNCHRON CX clinical system. Three different Synchron Control materials, each containing a different concentration of glucose (representing clinically low, normal, and high glucose levels), were measured.

Table 2 below lists the results of glucose measurements of five batches of the Synchron Control materials. Each value represents an average of measurements taken at 6 laboratories, each of which performed 6 measurements (a total of 36 measurements).

TABLE 2

Synchron Control Value Assignment Results for Glucose (in mg/dL)

| BATCH | GLUCOSE CONCENTRATION | CX OXIDASE | CX HEXOKINASE | LX OXIDASE | LX HEXOKINASE |
|---|---|---|---|---|---|
| 25 | Low | 42 | 45 | 43 | 46 |
| 26 | Low | 44 | 45 | 44 | 45 |
| 27 | Low | 43 | 44 | 44 | 45 |
| 28 | Low | 44 | 44 | 44 | 45 |
| 29 | Low | 43 | 45 | 44 | 45 |
| 25 | Normal | 216 | 230 | 224 | 234 |
| 26 | Normal | 219 | 227 | 225 | 232 |
| 27 | Normal | 210 | 223 | 219 | 222 |

TABLE 2-continued

Synchron Control Value Assignment Results for Glucose (in mg/dL)

| GLUCOSE BATCH | CONCENTRATION | CX OXIDASE | CX HEXOKINASE | LX OXIDASE | LX HEXOKINASE |
|---|---|---|---|---|---|
| 28 | Normal | 217 | 226 | 223 | 230 |
| 29 | Normal | 215 | 227 | 222 | 228 |
| 25 | High | 374 | 416 | 399 | 411 |
| 26 | High | 376 | 410 | 402 | 416 |
| 27 | High | 361 | 398 | 387 | 401 |
| 28 | High | 374 | 403 | 391 | 408 |
| 29 | High | 368 | 404 | 390 | 408 |

FIG. 2 shows the foregoing information in graphical form. As can be seen in FIG. 2, the inter-method relationships between the four instrument/method combinations (four methodologies), i.e. SYNCHRON LX/glucose oxidase test, SYNCHRON CX/glucose hexokinase test, SYNCHRON LX/glucose oxidase test, and SYNCHRON CX/glucose hexokinase test, are consistent from one batch to another.

Using the data shown in Table 2 above, the average glucose recovery concentration for each methodology was calculated for each batch of Synchron Control material. These averages are shown in Table 3 below.

TABLE 3

Average Synchron Control Glucose Recovery (in mg/dL)

| GLUCOSE CONCENTRATION | CX/OXIDASE METHOD | CX/ HEXOKINASE METHOD | LX/ OXIDASE METHOD | LX/ HEXOKINASE METHOD |
|---|---|---|---|---|
| Low | 43.2 | 44.6 | 44.0 | 45.0 |
| Normal | 215.4 | 226.6 | 221.3 | 226.7 |
| High | 371.0 | 406.2 | 389.3 | 405.7 |

The entries in each row of Table 3 were summed, and each entry in the row was expressed as a fraction of that sum. For example, the glucose concentration measured with a SYNCHRON CX instrument using glucose oxidase (43.2 mg/dL) was expressed as a fraction of the sum of the concentrations determined using all four methodologies, i.e. 43.2/(43.2+44.6+43.8+45.2), which equals 0.244. These fractions, the relative analyte recovery ratios, are shown in Table 4 below.

TABLE 4

Relative Synchron Control Glucose Recovery

| GLUCOSE CONCENTRATION | CX/OXIDASE METHOD | CX/ HEXOKINASE METHOD | LX/ OXIDASE METHOD | LX/ HEXOKINASE METHOD |
|---|---|---|---|---|
| Low | 0.244 | 0.252 | 0.249 | 0.255 |
| Normal | 0.242 | 0.255 | 0.249 | 0.255 |
| High | 0.236 | 0.258 | 0.248 | 0.258 |

Example 2

Comparison of Analyte Recovery Value Assignment Methods

The present method was assessed by retroactively analyzing analyte recovery data. Glucose recovery data for a batch of Synchron Control generated from tests performed at a laboratory was compared with data generated using the present method. Data from approximately 12 tests performed for each methodology at two laboratories was compared to the "true" recovery value determined for this batch of Synchron Control (i.e., the average recovery value from a larger data set). The bias for each value (i.e., the difference between the measured value and the true value) was determined, and the pooled standard deviation of the biases (i.e., the square root of the average of the squared standard deviations of the biases) for the data determined in this way is set out in Table 5 below under the heading "SD OF BIAS: OLD PROCESS." The pooled standard deviation is an estimate of process accuracy and reliability.

The present method was performed using data from the same batch of Synchron Control material. Data from the same 12 tests performed using each methodology was averaged to produce target sample concentration data, and such target sample concentration data was then multiplied by the appropriate relative analyte recovery ratio (set out in Table 4 above) in order to generate an estimated recovery value according to the present methods. The standard deviation of the bias and pooled standard deviation are set out in Table 5 below under the heading "SD OF BIAS: NEW PROCESS." As compared with the pooled standard deviation determined using the prior process, there is approximately a 20% improvement in the accuracy of the data generated by the present method.

TABLE 5

Comparison of Value Assignment Methods

| INSTRUMENT | METHOD | SD OF BIAS: OLD PROCESS | SD OF BIAS: NEW PROCESS |
|---|---|---|---|
| SYNCHRON CX | OXIDASE | 1.52 | 0.91 |
| SYNCHRON CX | HEXOKINASE | 0.54 | 0.70 |
| SYNCHRION LX | OXIDASE | 1.03 | 1.12 |
| SYNCHRION LX | HEXOKINASE | 1.04 | 0.78 |
| | POOLED SD: | 1.09 | 0.89 |

% IMPROVEMENT: 22.2%

Although the present invention has been discussed in considerable detail with reference to certain preferred embodiments, other embodiments are possible. The steps disclosed for the present methods are not intended to be limiting nor are they intended to indicate that each step depicted is essential to the method, but instead are exemplary steps only. Therefore, the scope of the appended claims should not be limited to the description of preferred embodiments contained in this disclosure. All references cited herein are incorporated by reference to their entirety.

What is claimed is:

1. A method of determining an assigned value corresponding to a concentration of an analyte in a target sample when measured using a first methodology, comprising the steps of:
    (a) determining a relative analyte concentration ratio by:
        (i) obtaining a first control sample concentration value, wherein the first control sample concentration value is determined by measuring the amount of the analyte in a control sample comprising the analyte using the first methodology;
        (ii) obtaining a second control sample concentration value, wherein the second control sample concentration value is determined by measuring the amount of the analyte in the control sample using a second methodology;
        (iii) adding the first control sample concentration value and the second control sample concentration value, thereby determining a summed control sample concentration value;
        (iv) dividing the first control sample concentration value by the summed control sample concentration value, thereby determining the relative analyte concentration ratio;
    (b) determining a summed target sample concentration value by:
        (i) obtaining a first target sample concentration value, wherein the first target sample concentration value is determined by measuring the amount of the analyte in the target sample using the first methodology;
        (ii) obtaining a second target sample concentration value, wherein the second target sample concentration value is determined by measuring the amount of the analyte in the target sample using the second methodology;
        (iii) adding the first target sample concentration value and the second target sample concentration value, thereby determining the summed target sample concentration value; and
    (c) determining the assigned value for the analyte in the target sample by multiplying the relative analyte concentration ratio and the summed target sample concentration value.

2. The method of claim 1, further comprising the steps of:
    obtaining a third control sample concentration value, wherein the third control sample concentration value is determined by measuring the amount of the analyte in the control sample using a third methodology, and wherein the summed control sample concentration value comprises the sum of the first control sample concentration value, the second control sample concentration value, and the third control sample concentration value; and
    obtaining a third target sample value, wherein the third target sample concentration value is determined by measuring the amount of the analyte in the target sample using the third methodology, and wherein the summed target sample concentration value comprises the sum of the first target sample concentration value, the second target sample concentration value, and the third target sample concentration value.

3. The method of claim 1, wherein the first methodology comprises a first analytical method performed with a first analytical instrument, and wherein the second methodology comprises the first analytical method performed with a second analytical instrument.

4. The method of claim 1, wherein the first methodology comprises a first analytical method performed with a first analytical instrument, and wherein the second methodology comprises a second analytical method performed with the first analytical instrument.

5. The method of claim 1, wherein the first methodology comprises a first analytical method performed with a first analytical instrument, and wherein the second methodology comprises a second analytical method performed with a second analytical instrument.

6. The method of claim 1, wherein the first control sample concentration value is an average of a plurality of values determined by measuring the amount of the analyte in the control sample a plurality of times using the first methodology.

7. The method of claim 6, wherein the analyte in the control sample is measured by a plurality of different testers.

8. The method of claim 7, wherein the analyte in the control sample is measured by at least six different testers.

9. The method of claim 1, wherein the second control sample concentration value is an average of a plurality of values determined by measuring the amount of the analyte in the control sample a plurality of times using the second methodology.

10. The method of claim 1, wherein the first methodology comprises an optical detection method.

11. The method of claim 1, wherein the first methodology comprises a nephelometric method.

12. The method of claim 1, wherein the first methodology comprises an electrochemical method.

13. The method of claim 1, wherein the first methodology comprises a first analytical instrument selected from the group consisting of a spectrophotometer, a colorimeter, a nephelometer, a polarimeter, a potentiometer, a voltmeter, and a fluorometer.

14. The method of claim 1, wherein the target sample comprises a material selected from the group consisting of urine, plasma, serum, blood, saliva, and cerebrospinal fluid.

15. The method of claim 1, wherein the analyte is selected from the group consisting of albumin, alanine aminotransferase, amylase, aspartate transferase, alkaline phosphatase, blood urea nitrogen, calcium, cholesterol, high-density lipoprotein cholesterol, creatinine kinase, creatinine, bilirubin, gamma-glutamyl transferase, glucose, iron, lactate dehydrogenase, magnesium, phosphorous, total iron binding capacity, total bilirubin, total protein, triglyceride GPO, uric acid, digoxin, gentamicin, phenobarbital, phenyloin, salicylate, theophylline, tobramycin, alcohol, ammonia, anti-streptolysin-O, cholinesterase, C-reactive protein, alpha-hydroxybutyrate dehydrogenase, lactate, leukocyte alkaline phosphatase, microprotein, pancreatic amylase, chloride, $CO_2$, potassium, sodium, IgA, IgG, IgM, trarsferrin, thyroxine, thyroxine-uptake, acetaminophen, acid phosphatase, amikacin, amphetamine, barbiturate, cannabinoid, carbamazepine, cocaine, ethosuximide, fibrinogen, fructosamine, lactate dehydrogenase-1, lidocaine, lipase, methadone, methaqualone, N-acetylprocainamide, opiate, phencyclidine, primidone, procainamide, propoxyphene, quinidine, valproic acid, and vancomycin.

16. The method of claim 1, wherein the analyte is a drug of abuse.

17. The method of claim 1, wherein the analyte is a therapeutic substance.

18. The method of claim 1, wherein the first methodology comprises an analytical method which involves the use of a reagent selected from the group consisting of bromcresol purple, Trinder's reagent, picrate, hexokinase, glucose oxidase, lactate oxidase, peroxidase, uricase, quinolinium dye, arsenazo III, ferrozine, pyridylazo dye, calmagite, formazan dye, molybdate, p-methylaminophenol, 2-amino-2-methyl-1-propanol, 2-chloro-4-nitrophenylmaltotrioside, dye amylopectin, monothioglycerol, N-acetylcysteine, pyruvate-lactate, and diglyceride.

19. The method of claim 1, wherein the target sample is adapted to be used in a diagnostic assay.

* * * * *